(12) United States Patent
Dodson

(10) Patent No.: US 6,343,515 B1
(45) Date of Patent: Feb. 5, 2002

(54) METHOD AND APPARATUS FOR IMPROVED MEASUREMENT OF TENSION AND COMPRESSION IN A WIRELINE

(75) Inventor: Steve W. Dodson, Logo Vista, TX (US)

(73) Assignee: Martin-Decker Totco, Cedar Park, TX (US)

( * ) Notice: Subject to any disclaimer, the term of this patent is extended or adjusted under 35 U.S.C. 154(b) by 0 days.

(21) Appl. No.: 09/476,861

(22) Filed: Jan. 3, 2000

Related U.S. Application Data

(63) Continuation-in-part of application No. 09/109,785, filed on Jul. 2, 1998, now abandoned.

(51) Int. Cl.[7] .............................................. G01N 3/08
(52) U.S. Cl. ...................................... 73/831; 73/862.46
(58) Field of Search .......................... 73/826, 828, 831, 73/862.451, 862.453, 862.46, 862.471, 862.473, 862.474

(56) References Cited

U.S. PATENT DOCUMENTS

| | | | | |
|---|---|---|---|---|
| 1,380,818 A | * | 6/1921 | McGrown | 73/862.451 |
| 4,509,376 A | * | 4/1985 | Thomasson | 73/862.56 |
| D297,818 S | * | 9/1988 | Tell | 73/862.451 |
| 4,989,450 A | * | 2/1991 | Shoberg et al. | 73/158 |
| 4,992,778 A | * | 2/1991 | McKeen et al. | 340/668 |

FOREIGN PATENT DOCUMENTS

| | | | | |
|---|---|---|---|---|
| GB | 2 063 494 A | * | 6/1919 | 73/862.474 |

* cited by examiner

*Primary Examiner*—Max Noori

(57) ABSTRACT

A tension measuring device including an elongated body having two ends and a deflection block secured to each end of the elongated body for holding a line spaced apart from the elongated body. The deflection blocks are positioned equidistant from a center of the elongated body. A clamping mechanism between the deflection blocks clamps the line to the elongated body wherein increased tension in the line will bend the elongated body. A strain gage element is connected to the elongated body for producing an output signal proportional to the bending of the elongated body. The strain gage element is positioned on the elongated body and is applied directly to the bending of the elongated body. A linearizing signal device is connected to the strain gage element for processing the output signal and for providing a readable output representative of the tension on the line. The linearizing signal device provides for linearization of the output signal from the strain gage element and is, for example, a capacitive circuit or a linear signal processor. A line tension readout device is adapted to receive and display the readable output representative of the tension of the line.

25 Claims, 5 Drawing Sheets

METHOD AND APPARATUS FOR IMPROVED MEASUREMENT OF TENSION AND COMPRESSION IN A WIRELINE

This patent application is a continuation-in-part of patent application Ser. No. 09/109,785 by Steven W. Dodson, filed Jul. 2, 1998, now abandoned, entitled Tension Measuring Device.

BACKGROUND OF THE INVENTION

1. Field of the Invention

This invention relates to the field of measuring tension in a line, particularly for use on wirelines on drilling rigs.

2. Description of the Related Art

A drilling or workover rig as used in oil and gas exploration includes a derrick, draw works, surface equipment and a wireline used to moveably suspend a drill string from the rig. The wireline is usually a wire rope or steel cable, although other materials have also been used. The well drill string, even in a moderately deep well is highly flexibly and relatively to damage. Controlling the drill string weight applied to the drill bit is very important in drilling efficiency. The wireline at one end is wound on a drum or windless and is then passed in several turns between a crown block and a traveling block. The other end of the wireline is secured at the rig foundation or base. The traveling block carries a hook with a rotary connection to a kelly. The hook supports the weight of the drill string within the wellbore and as applied to the drill bit.

The wireline or cable is typically multistrand with multi-wires per strand. For example, a cable or wireline of one and one-eighth inch diameter can have a fiber core surrounded by eight strands each having nineteen steel wires. This wireline has a breaking strength of about forty tons but yet is pliable and wear resistant. Although the wirelines handle large loads, there is a finite load limit wherein breaking problems can occur. The tension conditions on the wireline in virtually every drilling rig is monitored. Various tension measuring devices have been employed to control the drill string weight on the drill bit and to indicate to the driller the tension conditions on the wireline. Typically, the wireline tension is measured using hydraulic tension transducers which are highly non-linear and temperature dependent. Modified strain gages are also used including a hydraulic sensor modified to accept a strain gage load cell in place of a hydraulic diaphragm which are very expensive to manufacture. Typical strain gauges are also susceptible to error due to temperature variations and mounted such that they are subject to physical harm due to contamination by the operating environment. Accordingly, a tension measuring device is needed which is simple to use and inexpensive to manufacture, and which also provides a linear output response signal which can be protected from the environment and temperature-compensated for temperature variation.

SUMMARY OF THE INVENTION

The system of the present invention including a tension measuring device mounted on a line, for example, a wireline on a drilling rig, wherein the tension measuring device is mounted between the wireline load and anchor ends. The tension measuring device includes an elongated body having two ends and a deflection block secured to each end of the elongated body for holding the wireline spaced apart from the elongated body. A clamping mechanism between the deflection blocks clamps the wireline to the elongated body wherein increased tension in the wireline will bend the elongated body. A pair strain gage elements are mounted inside of the elongated body for producing an output signal proportional to the bending of the elongated body. The strain gage element is, for example, positioned inside of the elongated body and is applied directly to the measure the tension and compression forces encountered during bending of the elongated body. The strain gauge bridge provides increased accuracy in calculating tension on a wire line by enabling calculation of tension by measurement of the tension and compression components. The strain gauge bridge also provides temperature compensation to enhance the accuracy of tension calcuations. The elongated body is hermetically sealed to protect the strain gauge from the elements. A linearizing signal device, for example, positioned within the elongated body, is connected to the strain gage element for processing the output signal and for providing a readable output representative of the tension on the wireline. The linearizing signal device provides for linearization of the output signal from the strain gage element and is, for example, a capacitive circuit or a linear signal processor. A wireline tension readout device is adapted to receive and display the readable output representative of the tension on the wireline.

Examples of the more important features of the invention thus have been summarized rather broadly in order that the detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DETAILED DESCRIPTION OF THE PREFERRED EMBODIMENTS

Figure 1:
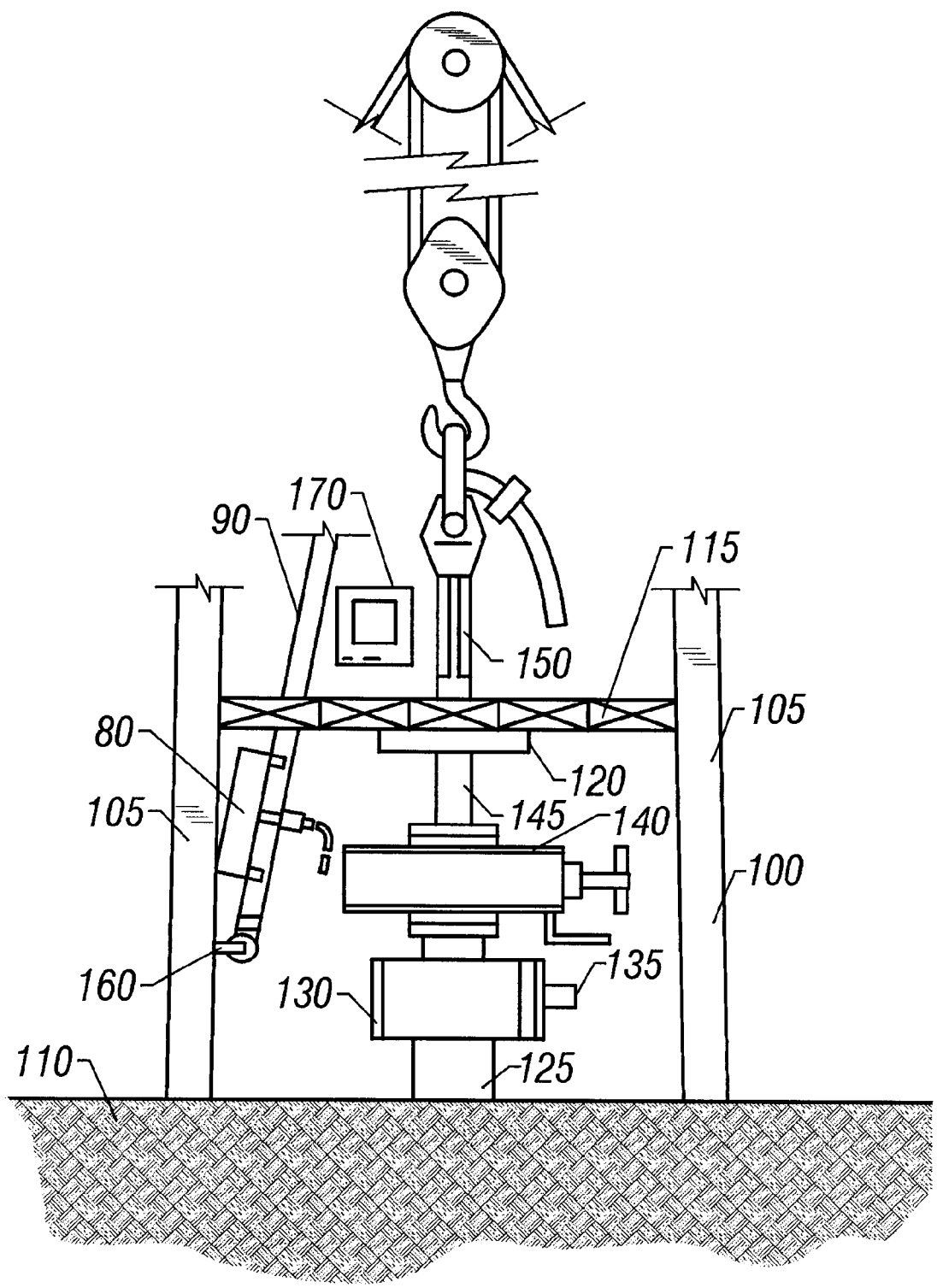
FIG. 1 is a perspective view of a rig floor of an oil well rotary rig wherein the line tension transducer of the present invention is mounted on a wireline.

A preferred embodiment of the present invention is illustrated in FIG. 1 wherein a wireline tension measuring device 80 according to the present invention is attached to a steel cable line or wireline 90 used, for example, with an oil well rotary rig 100. The rig 100 includes beam supports, such as legs 105, which rest upon the earth's surface 110, and which support the machinery and operating elements required to drill an oil well. A floor 115 is provided between the legs 105 of the rig 100. The floor 115 is located about a drive table 120 and supporting equipment used in carrying out the drilling operation. The drive table 120 is positioned above a well casing 125 and usually cemented within the earth's formations for about fifteen hundred (1,500) feet at the upper portion of the wellbore. The casing 125 carries a mud head assembly 130 wherein the returning drilling mud is moved by a conduit 135 to the mud reconditioning system. Above the mud head 130 is mounted a blow out preventer 140.

The drill string 145 passes downwardly from the drive table 120 through the blow out preventer 140 through the casing 125 and into the wellbore. Mounted atop the drill string 145 and extending through the drive table 120 is a kelly 150 which engages the drive surfaces within the drive table 120 and rotates the drill string 145 in the wellbore. The kelly 150 is a heavy squared or hexagonal steel member and is supported from a crown block (not shown) at the rig 100 by a plurality of wireline loops extending to a traveling block carrying a hook (not shown) which is connected by a swivel joint to the top of the kelly 150. The kelly 150 includes a bored passageway that permits fluid to be circulated from the swivel into the drill stem and up the annulus or vice-versa.

On one end, the wireline 90 is power rotated, by a windless, wherein the drill string 145 is raised and lowered within the wellbore. The anchor end of the wireline 90 is secured to the rig 100, for example, through a shackle 160 secured by an anchor means. The wireline tension measuring device 80 of the present invention may be mounted on the wireline 90 between the wireline's 90 load and anchor ends at any convenient location on the rig 100 such as beneath the floor 115. The wireline tension measuring device 80 of the present invention is a clamp-on device including strain gage elements producing an output signal representing the wireline loads for calculation of hook load and weight on bit ("WOB"). The WOB and the amount of weight supported by the hook, the hook load, which is reflected by the tension exerted upon the wireline 90 by the wright of the drill string 145 is critical knowledge during drilling operations. The tension on the wireline 90 is measured by the tension measuring device 80 mounted, for example, on the wireline 90 adjacent the anchored end at shackle 160 as illustrated in FIG. 1.

The tension measuring device 80 is connected by suitable signal lines (not shown) to a wireline tension readout device 170 adapted to receive and display the readable output representative of the tension conditions on the wireline 90. The readout device 170 is, for example, mounted on the floor 115 of the rig 100. The readout device 170 includes, for example, a computer readout or pressure gages indicating the total magnitude of tension exerted on the wireline 90 and the magnitude of change in the tension conditions. The wireline tension measuring device 80 may also be used to control the movement of the wireline 90 by controlling the windless. The driller operating the machinery associated with the rig 100 can select and monitor the tension conditions with the wireline tension readout device 170.

Figure 2:
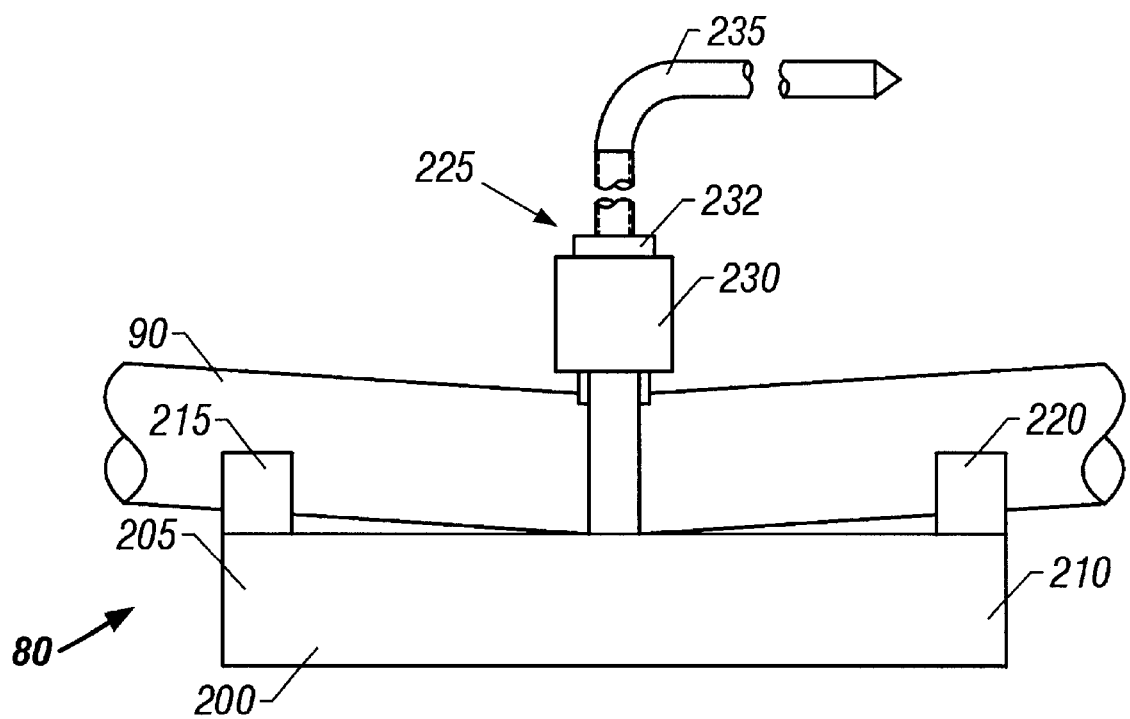
FIG. 2 is a side view of the line tension transducer of the present invention.
Figure 3:
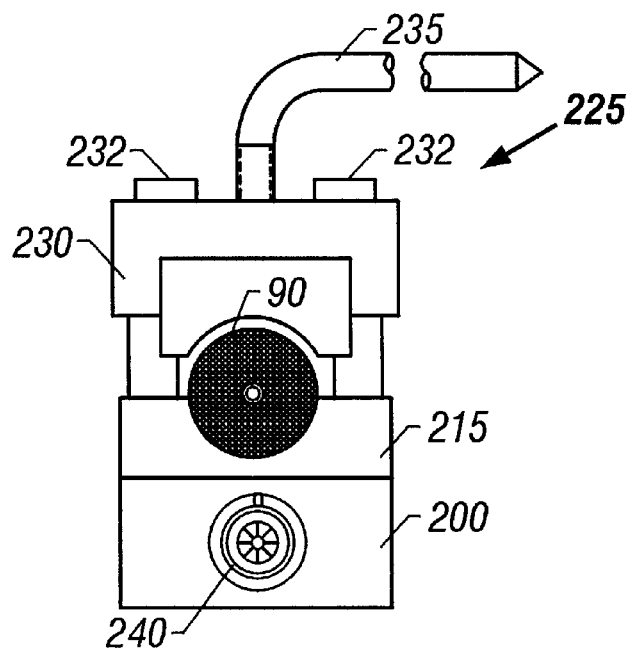
FIG. 3 is an end view of the line tension transducer of the present invention.
Figure 4:
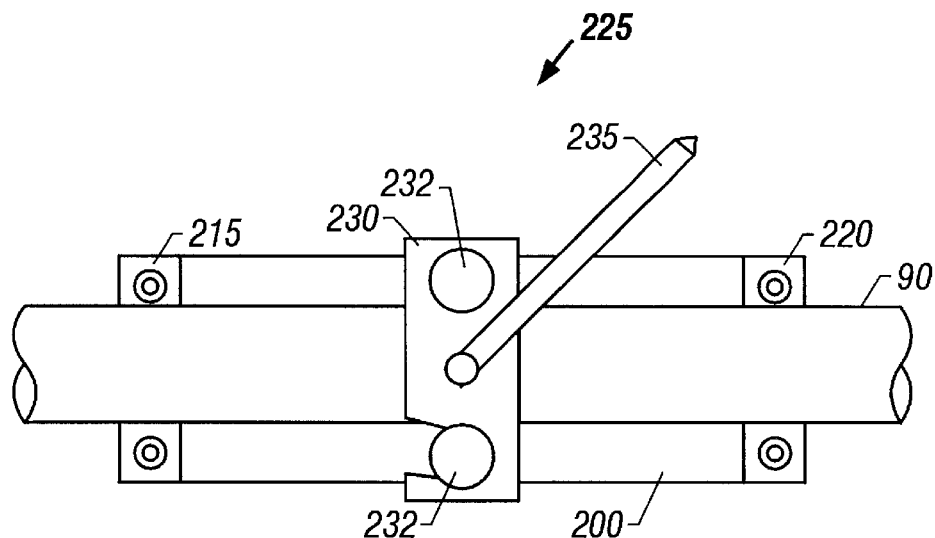
FIG. 4 is a plan view of the line tension transducer of the present invention.

Referring now to FIGS. 2 through 4, the tension measuring device 80 is illustrated in greater detail. The tension measuring device 80 includes an elongated body 200 having two ends 205 and 210, respectively and longitudinally oriented on the wireline 90. A deflection block 215 and 220 is secured to each end 205 and 210, respectively, of the elongated body 200 and, preferably, positioned equidistant from a center of the elongated body 200 for holding the wireline 90 spaced apart from the elongated body 200. A clamping mechanism 225 is positioned between the deflection blocks 215 and 220, respectively, for clamping the wireline 90 to the elongated body 200 and wherein increased tension in the wireline 90 will bend the elongated body 200. The clamping mechanism 225 includes a yoke 230 and crank lever 235. The yoke 230 is positioned centrally on the elongated body 200 and held in place with screws 232. The crank lever 235 is tightened to capture the wireline 90 between the yoke 230 and the elongated body 200. The clamping mechanism 225 is assembled such that no parts become detached during mounting and installation on the wireline 90 and the crank lever 235 makes additional tools during installation unnecessary.

As seen in FIGS. 2 and 3, the clamping mechanism 225 and deflection blocks 215 and 220 are arranged so as to depress the wireline 90 laterally a certain distance towards the elongated body 200. When the clamping mechanism 225 is installed and clamping pressure applied, the deflection blocks 215 and 220 and clamping mechanism 225 cause an initial deflection of the wireline 90, for example, approximately one-quarter (¼) inch. When additional load is applied to the wireline 90, the wireline 90 tends to straighten at the deflection points and exerts an outward force on the clamping mechanism 225. The clamping mechanism 225 then transfers increased tension in the wireline 90 to the elongated body 200 to bend the elongated body 200. The bending of the elongated body 200 correlates to the tension in the wireline 90 and is sensed by a strain gage element 250 (illustrated in FIG. 5), preferably, applied directly to the bending of the elongated body 200. The strain gage element 250, for example, a strain gage bridge, is positioned on and connected to the elongated body 200 for producing an output signal proportional to the bending of the elongated body 220. The elongated body 200 and strain gage element 250 are positioned, for example, such that a full 5,000 ohm strain gage bridge will produce 1 mV/V output at a rated load of 100,000 pounds.

The elongated body 200 preferably consists of a beam having a center bore. A pin connector 240 used for a signal interface may be located at one end of the elongated body 200 (shown in FIG. 3), or on a side of the elongated body 200. The strain gage 250 is positioned on an inner surface of the elongated body 200 and applied directly to sense bending stress in the elongated body 200. Other electronics may also be housed in the hollow cross-section of the elongated body 200, for example, a sensor amplification device or a data acquisition unit for driving the sensor.

Figure 5:
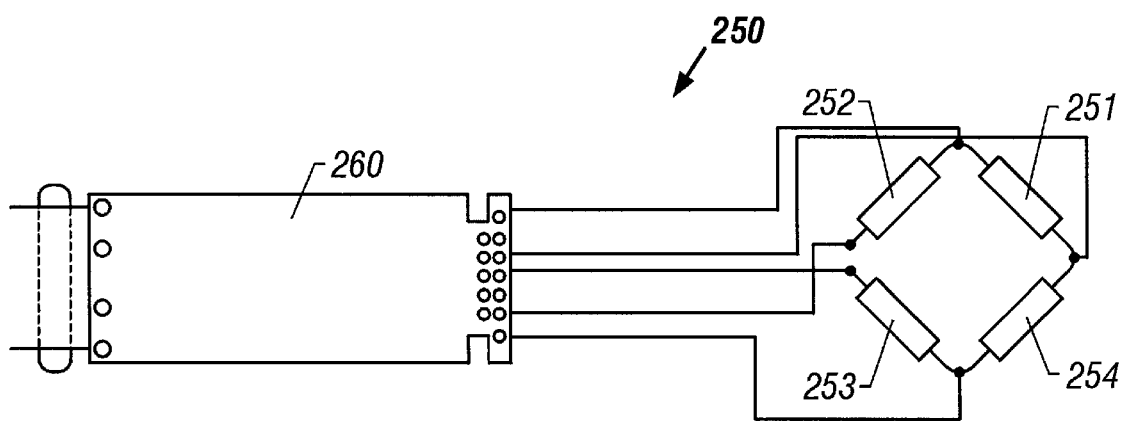
FIG. 5 is a simplified schematic diagram of one embodiment of a portion of the electrical circuit for a linearized measured output of the wireline tension including a strain gage and a linear signal processor.
Figure 6:
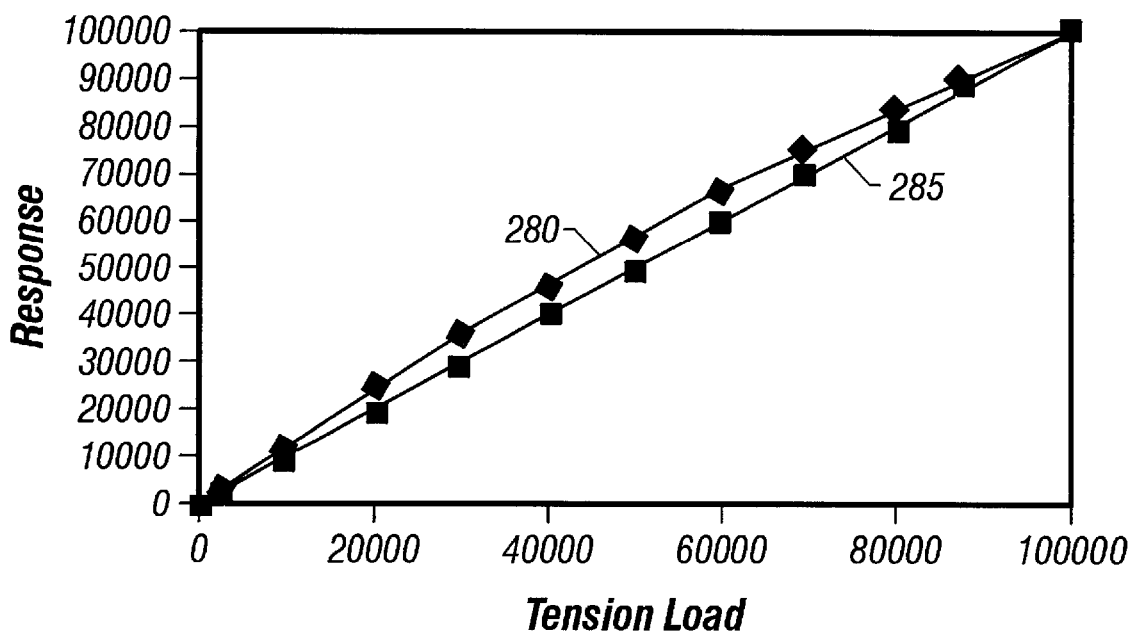
FIG. 6 is a chart illustrating a linearized output of the tension measuring device according to the present invention.

A linearizing signal device 260, shown in FIG. 5, is connected to the strain gage 250 for processing the output signal and for providing a readable output representative of the tension of the wireline 90. In one embodiment, the linearizing signal device 260 is a capacitive circuit for providing linearization to the output signal from the strain gage element 250. In another embodiment, the linearizing signal device 260 is a linear signal processor for providing linearization to the output signal from the strain gage element 250. The linearizing signal device 260 is preferably accomplished using a "smart" signal device rather than performing linearizing calibrations later in the data acquisition. FIG. 6 is a chart illustrating an output response before the linearizing signal device 260 is applied and the linearized signal output response of the line tension transducer 80 according to the present invention.

Figure 7:
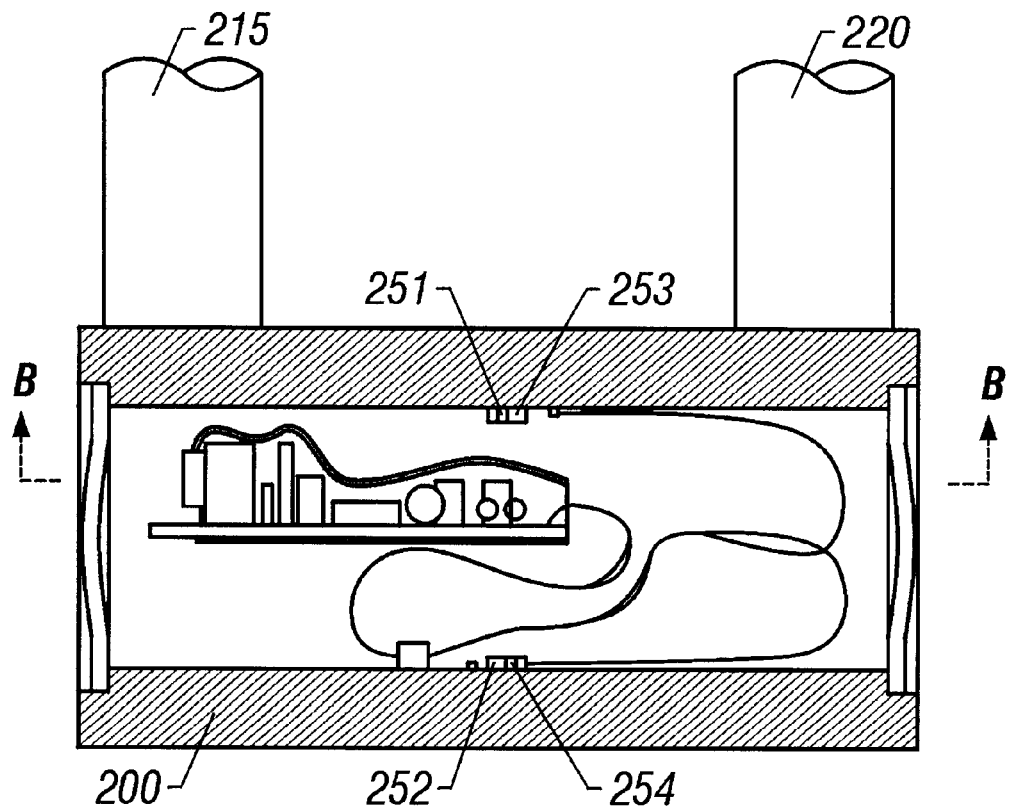
FIG. 7 is a side view of the elongated body of the present invention illustrating the preferred placement of strain gauges for measuring tension and compression in a preferred embodiment of the present invention.

Turning now to FIG. 7, a preferred embodiment of the present invention is illustrated showing the preferred position of the strain gauges 251, 252, 253 and 254. FIG. 7 shows the strain gauges under load wherein strain gauges 251 and 253 are in tension under load and strain gauges 252 and 254 in compression under load.

Figure 8:
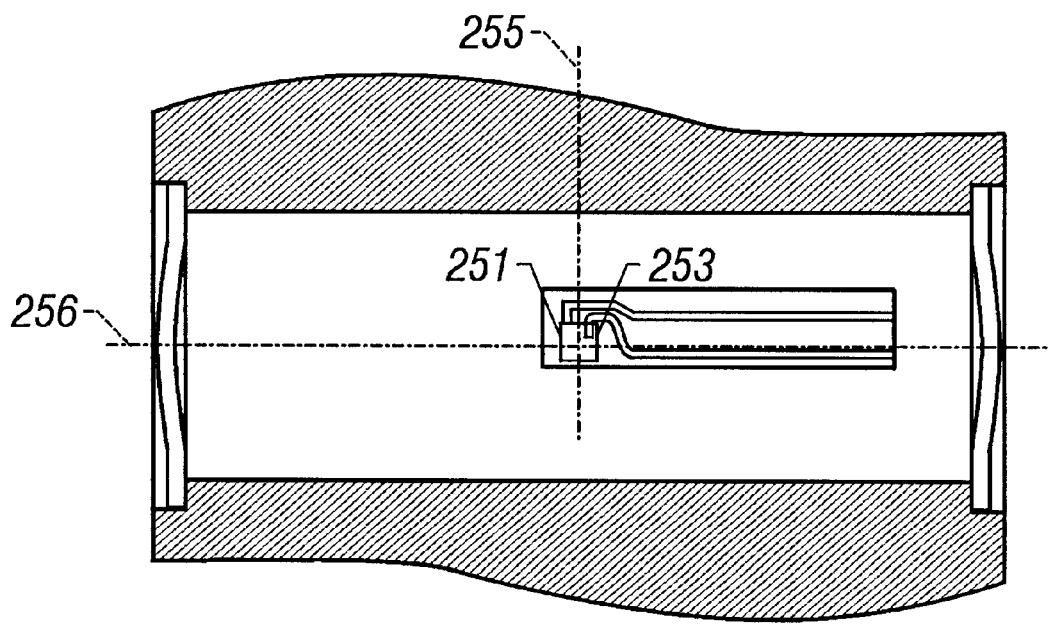
FIG. 8 is a top view of the elongated body of the present invention illustrating the preferred placement of strain gauges for measuring tension and compression in a preferred embodiment of the present invention.

Turning now to FIG. 8, a preferred embodiment of the present invention is illustrated showing the preferred position of strain gauges 251 and 253. As shown in FIG. 8, strain gauges 251 and 253 are mounted on the inside wall of elongated body 200 which is adjacent wireline 90. Strain gauges 251 and 253 are centered on the centerline 256 which is contained in a plane containing a line passing through the longitudinal axis of elongated body 200 and also passing through the longitudinal axis wireline 90. Strain gauges 251 and 253 are also centered along centerline 255 which is equidistant from each end of elongated body 200. This arrangement of strain gauges 251 and 253 enables wireline 90 to place strain gauges 251 and 253 under tension.

Strain gauges 252 and 254 are similarly mounted on an inside wall of elongated body 200, however, on the inside wall of elongated body 200 which is opposite wireline 90 and opposite strain gauges 251 and 253. Strain gauges 251 and 253 are also aligned along centerline 256 which is contained in a plane formed by a line passing through the longitudinal axis of elongated body 200 and wireline 90. Strain gauges 251 and 253 are also centered along centerline 255 which is equidistant from each end of elongated body 200. This arrangement of strain gauges 252 and 254 enables wireline 90 to place strain gauges 252 and 254 under compression.

The location of the strain gauges 251, 252, 253 and 254 enables measurement of tension and compression exerted by wireline 90 thereby enabling enhanced accuracy in the calculation of tension exerted on wireline 90. There are four signal derived from strain gauges 251, 252, 253 and 254. Two compression signals, one each from strain gauge 252 and 254 and two tension signals, one each from tension signals 251 and 253. These four signals are utilized to calculate the tension on wireline 90. In a preferred embodiment, the four signals are added together to obtain an enhanced accuracy signal The use of strain gauge bridges formed by strain gauge elements 251, 252, 253 and 254 also increases accuracy of tension calculation and measurements by providing temperature compensation. Moreover, the location of the strain gauges 251, 252, 253 and 254 inside of the elongated body 200 provides for protection against damage from contact and provides a hermetically sealed environment for the strain gauge elements.

The tension measuring device of the present invention provides a simple clamp on installation on any line requiring no additional tools during installation and is easily portable. Typically, wireline tension is measured using hydraulic tension transducers which are highly non-linear and temperature dependent. Modified strain gages are also used including a hydraulic sensor modified to accept a strain gage load cell in place of a hydraulic diaphragm, which are very expensive to manufacture. The tension measuring device of the present invention provides a simple to use and inexpensive to manufacture device which also provides a linear output response signal.

While preferred embodiments have been shown and described, various modifications and substitutions may be made thereto without departing from the spirit and scope of the invention. Accordingly it is to be understood that the present invention has been described by way of illustrations and not limitations.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. A tension measuring device comprising:
   (a) an elongated body having two ends, said elongated body further comprising a hollow interior comprising a first interior wall and a second interior wall, wherein the first interior wall and the second interior wall oppose each other;
   (b) a deflection block secured to each end of the elongated body for holding a line spaced apart from the elongated body;
   (c) a clamping mechanism between the deflection blocks from clamping the line to the elongated body wherein increased tension in the line will bend the elongated body;
   (d) a first strain gauge element attached to the first interior wall and a second strain gauge element attached to the second interior wall, wherein the first strain gauge produces an output signal proportional to the bending tension of the first interior wall of the elongated body and the second strain gauge produces an output signal proportional to the compression of the second interior wall; and
   (e) a linearizing signal device connected to the first and second strain gauge elements for processing the output signal and for providing a readable output representative of the tension on the line.

2. A tension measuring device as recited in claim 1, wherein the linearizing signal device is a capacitive circuit.

3. A tension measuring device, as recited in claim 1, wherein the linearizing signal device is a linear signal processor.

4. A tension measuring device, as recited in claim 1, wherein the elongated body comprises a beam having a hollow cross-section.

5. A tension measuring device, as recited in claim 4, wherein the strain gauge bridge further comprises another strain gauge mounted on a second inside wall of the elongated further comprises another strain gauge mounted on a second inside wall of the elongated housing, the second inside wall being opposite the fist inside wall of the elongated housing.

6. A tension measuring device, as recited in claim 5, wherein the strain gauge bridge measures tension and compression.

7. A tension measuring device, as recited in claim 1, wherein the strain gauge bridge measures both tension and compression of the elongated body caused by tension on the line.

8. A tension measuring device, as recited in claim 7, wherein the strain gage bridge comprises a pair of strain gages positioned on an inner surface of the elongated body and wherein the strain gage is applied directly to bending of the elongated body.

9. A tension measuring device, as recited in claim 7, wherein the linearizing signal device is positioned within the hollow cross-section of the elongated body.

10. A tension measuring device, as recited in claim 1, wherein the strain gauges are positioned equidistant from a center of the elongated body.

11. A system for measuring tension on a wireline comprising:
   (a) tension measuring device mounted on the wireline between the wireline load and anchor ends including:
      (i) an elongated body having two ends, said elongated body further comprising a hollow interior comprising a first interior wall and a second interior wall, wherein the first interior wall and the second interior wall oppose each other;
      (ii) a deflection block secured to each end of the elongated body for holding the wireline spaced apart from the elongated body;
      (iii) a clamping mechanism between the deflection blocks for clamping the wireline to the elongated body wherein increased tension in the wireline will bend the elongated body; and
      (iv) a first strain gauge element attached to the first interior wall and a second strain gauge element attached to the second interior wall, wherein the first strain gauge produces an output signal proportional to the bending tension of the elongated body and the second strain gauge element produces an output signal proportional to the compression of the second interior wall;
   (b) a linearizing signal device connected to the first and second strain gauge elements for processing the output signal and for providing a readable output representative of the tension on the wireline; and
   (c) a wireline tension readout device adapted to receive and display the readable output representative of the tension on the wireline.

12. A system, as recited in claim 11, wherein the linearizing signal device is a capacitive circuit.

13. A system, as recited in claim 1, wherein the linearizing signal device is a linear signal processor.

14. A system, as recited in claim 11, wherein the elongated body is a beam having a center bore.

15. A system, as recited in claim 14, wherein the strain gage is positioned on an inner surface of the elongated body and wherein the strain gage element is applied directly to the bending of the elongated body.

16. A system, as recited in claim 11, wherein the linearizing signal device is positioned within the hollow cross-section the elongated body.

17. A system, as recited in claim 11, wherein the deflection blocks are positioned equidistant from a center of the elongated body.

18. A tension measuring device for providing an indication of tension in a wireline comprising:
   (a) a beam having two ends and a hollow cross-section;
   (b) a deflection block secured to each end of the beam and positioned equidistant from a center of the beam for holding the wireline spaced apart from the beam;
   (c) a clamping mechanism between the deflection blocks for clamping the wireline to the bean wherein increased tension in the wireline will bend the beam;
   (d) a strain gauge bridge applied directly to the bending of the beam and positioned on opposing inner surfaces of the beam for producing output signals proportional to the bending tension and compression of the beam; and
   (e) a capacitive circuit positioned within the hollow cross-section of the beam and connected to the strain gauge bridge for processing the output signals and for providing a linearized readable output representative of the tension on the wireline.

19. A tension measuring device, as recited in claim 18, further comprising:
   (a) a readout device adapted to receive and display the linearized readable output.

20. A tension measuring device for providing an indication of tension in a wireline comprising:
   (a) a beam having two ends and a hollow cross-section;
   (b) a deflection block secured to each end of the beam and positioned equidistant from a center of the beam for holding the wireline spaced apart from the beam;
   (c) a clamping mechanism between the deflection blocks for clamping the wireline to the beam wherein increased tension in the wireline will bend the beam;
   (d) a strain gauge bridge applied directly to the bending of the beam and positioned on opposing inner surfaces of the beam for producing output signals proportional to the bending tension and compression of the inner surfaces of the beam; and
   (e) a linear signal processor positioned within the hollow cross-section of the beam and connected to the strain gauge bridge for processing the output signals and for providing a linearized readable output representative of the tension on the wireline.

21. A tension measuring device, as recited in claim 20, further comprising:
   (a) a readout device adapted to receive and display the linearized readable output.

22. The system of claim 9 wherein the strain gauge elements are temperature compensated.

23. The system of claim 16 wherein the strain gauge elements are temperature compensated.

24. The system of claim 18 wherein the strain gauge elements are temperature compensated.

25. A tension measuring device, as recited in claim 1, wherein the strain gauge elements are temperature compensating.

* * * * *